(12) United States Patent
Miyoshi et al.

(10) Patent No.: US 8,330,846 B2
(45) Date of Patent: Dec. 11, 2012

(54) IMAGE PICKUP APPARATUS

(75) Inventors: Takashi Miyoshi, Atsugi (JP); Akio Kosaka, Hachioji (JP); Hidekazu Iwaki, Hachioji (JP); Takayoshi Togino, Koganei (JP)

(73) Assignee: Olympus Corporation, Tokyo (JP)

( * ) Notice: Subject to any disclaimer, the term of this patent is extended or adjusted under 35 U.S.C. 154(b) by 516 days.

(21) Appl. No.: 12/345,043

(22) Filed: Dec. 29, 2008

(65) Prior Publication Data

US 2009/0147126 A1 Jun. 11, 2009

Related U.S. Application Data

(63) Continuation of application No. PCT/JP2007/063163, filed on Jun. 29, 2007.

(30) Foreign Application Priority Data

Jun. 30, 2006 (JP) .................................. 2006-182519

(51) Int. Cl.
*H04N 5/225* (2006.01)
*H04N 7/14* (2006.01)

(52) U.S. Cl. .................................... 348/335; 348/14.16

(58) Field of Classification Search .................... 348/49, 348/50, 169–172, 369, 14.6, 333.03, 14.61
See application file for complete search history.

(56) References Cited

U.S. PATENT DOCUMENTS

| 6,211,903 | B1 * | 4/2001 | Bullister .................... 348/14.16 |
| 7,507,201 | B2 * | 3/2009 | Rovegno ........................ 600/111 |
| 2003/0234867 | A1 * | 12/2003 | Fujita et al. ................ 348/207.1 |
| 2004/0196433 | A1 | 10/2004 | Durnell | |
| 2009/0040461 | A1 * | 2/2009 | Efron et al. .................... 351/210 |

FOREIGN PATENT DOCUMENTS

| JP | 1-185241 A | 7/1989 |
| JP | 2004-181233 A | 7/2004 |
| JP | 2005-500630 A | 1/2005 |
| JP | 3114698 U | 8/2008 |

OTHER PUBLICATIONS

International Preliminary Report on Patentability and Written Opinion dated Jan. 29, 2009 (5 pages), issued in counterpart International Application PCT/JP2007/063163.

* cited by examiner

*Primary Examiner* — Nicholas Giles
*Assistant Examiner* — Abdelaaziz Tissire
(74) *Attorney, Agent, or Firm* — Holtz, Holtz, Goodman & Chick, PC

(57) ABSTRACT

An image pickup apparatus is provided with an imaging optical system (imaging lens), an image sensor for picking up a subject image formed by the imaging optical system, and a view division optical system (first mirror) which divides a view picked up by the image sensor into an environment imaging side view and an eyeball imaging side view.

19 Claims, 12 Drawing Sheets

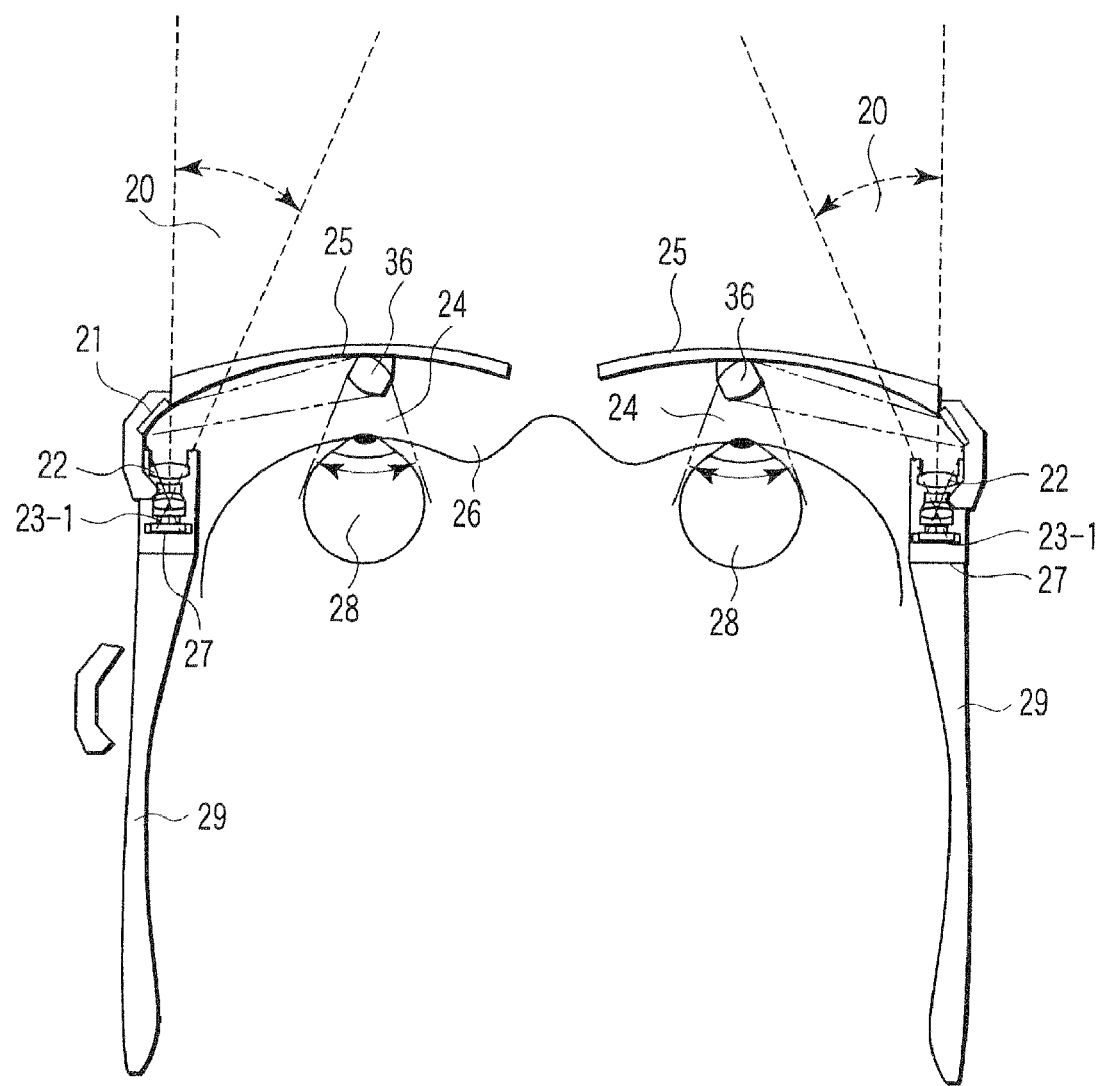
F I G. 20

IMAGE PICKUP APPARATUS

CROSS REFERENCE TO RELATED APPLICATIONS

This is a Continuation Application of PCT Application No. PCT/JP2007/063163, filed Jun. 29, 2007, which was published under PCT Article 21(2) in Japanese.

This application is based upon and claims the benefit of priority from prior Japanese Patent Application No. 2006-182519, filed Jun. 30, 2006, the entire contents of which are incorporated herein by reference.

BACKGROUND OF THE INVENTION

1. Field of the Invention

The present invention related to an image pickup apparatus, and more particularly, to an image pickup apparatus in which an environmental image and an eyeball image can be picked up by means of a single image sensor.

2. Description of the Related Art

Conventionally known is an image pickup apparatus that is configured to image-acquire both the front of a mounter and an eyeball. An image processing method is proposed in, for example, JPN. PAT. Appln. KOKAI Publication No. 2004-181233, in which an important area in an image is determined by measuring the line of sight and the pupil diameter by means of an eyeball image acquisition camera that is mounted on a pair of glasses.

BRIEF SUMMARY OF THE INVENTION

According to the prior art technique, a scene image and an eyeball image are caught by means of a plurality of cameras, so that the apparatus cannot be easily reduced in size and weight. Further, the apparatus, for use as a wearable camera that is continually mounted on a human body, requires much power consumption and cannot cope with the problem of prolonged drive.

The present invention had been made in consideration of these circumstances, and its object is to provide an image pickup apparatus capable of picking up an environmental image and an eyeball image while reducing the number of cameras used.

In order to obtain the above object, according to a first embodiment of the present invention, there is provided an image pickup apparatus comprising:
an imaging optical system;
an image sensor for picking up a subject image formed by the imaging optical system; and
a view division optical system which divides a view picked up by the image sensor into an environment imaging side view and an eyeball imaging side view.

According to a second embodiment of the present invention, there is provided an image pickup apparatus according to a first embodiment, wherein the view division optical system is a reflective mirror which is located prior to the imaging optical system at a predetermined inclination to the imaging optical system and divides the view of the imaging optical system into at least two parts.

According to a third embodiment of the present invention, there is provided an image pickup apparatus according to a second embodiment, wherein the reflective mirror is formed of an optical system with negative power.

According to a fourth embodiment of the present invention, there is provided an image pickup apparatus according to a third embodiment, wherein the reflective mirror is a convex mirror.

According to a fifth embodiment of the present invention, there is provided an image pickup apparatus according to a third embodiment, wherein the reflective mirror is as transmissive-reflective mirror lens having a concave refractive surface and at least a reflective surface with a radius of curvature larger than that of concave refractive surface.

According to a sixth embodiment of the present invention, there is provided an image pickup apparatus according to a second embodiment, wherein the reflective mirror is formed of an optical system with positive power.

According to a seventh embodiment of the present invention, there is provided an image pickup apparatus according to a sixth embodiment, wherein the reflective mirror is a concave mirror.

According to an eighth embodiment of the present invention, there is provided an image pickup apparatus according to a sixth embodiment, wherein the reflective mirror is a transmissive-reflective mirror lens having a convex refractive surface and at least a reflective surface with a radius of curvature smaller than that of the convex refractive surface.

According to a ninth embodiment of the present invention, there is provided an image pickup apparatus comprising;
an imaging optical system;
an image sensor for picking up a subject image formed by the imaging optical system;
a view division optical system which divides a view picked up by the image sensor into an environment imaging side view and an eyeball imaging side view; and
a bent optical system for picking up the image from the front of an eyeball based on the view divided by the view division optical system.

According to a tenth embodiment of the present invention, there is provided an image pickup apparatus according to a ninth embodiment, wherein the view division optical system is a reflective mirror which is located prior to the imaging optical system at a predetermined inclination to the imaging optical system and divides the view of the imaging optical system into at least two parts, and the bent optical system is a reflective mirror which further bends the halved view at a predetermined angle.

According to an eleventh embodiment of the present invention, there is provided an image pickup apparatus comprising:
a first image pickup apparatus including a first imaging optical system, a first image sensor for picking up a subject image formed by the first imaging optical system, and a first view division optical system which divides a view picked up by the first image sensor into an environment imaging side view and an eyeball imaging side view; and
a second image pickup apparatus including a second imaging optical system, a second image sensor for picking up a subject image formed by the second imaging optical system, and a second view division optical system which divides a view picked up by the second image sensor into an environment imaging side view and an eyeball imaging side view,
the first image pickup apparatus and the second image pickup apparatus being located opposite each other so that one is configured to pick up an image of the other.

According to a twelfth embodiment of the present invention, there is provided an image pickup apparatus according to an eleventh embodiment, wherein at least one of the first image pickup apparatus and the second image pickup apparatus is furnished with a marker for detecting a positional fluctuation between the first image pickup apparatus and the second image pickup apparatus.

BRIEF DESCRIPTION OF THE SEVERAL VIEWS OF THE DRAWING

FIG. 20 is a horizontal sectional view of a head-mounted camera according to a sixth embodiment of the present invention.

DETAILED DESCRIPTION OF THE INVENTION

Embodiment of the present invention will now be described with reference to the accompanying drawings. The following is a description of a case where an image pickup apparatus according to the present invention is applied to a head-mounted camera with an eyeball image acquisition function.

First Embodiment

Figure 1:
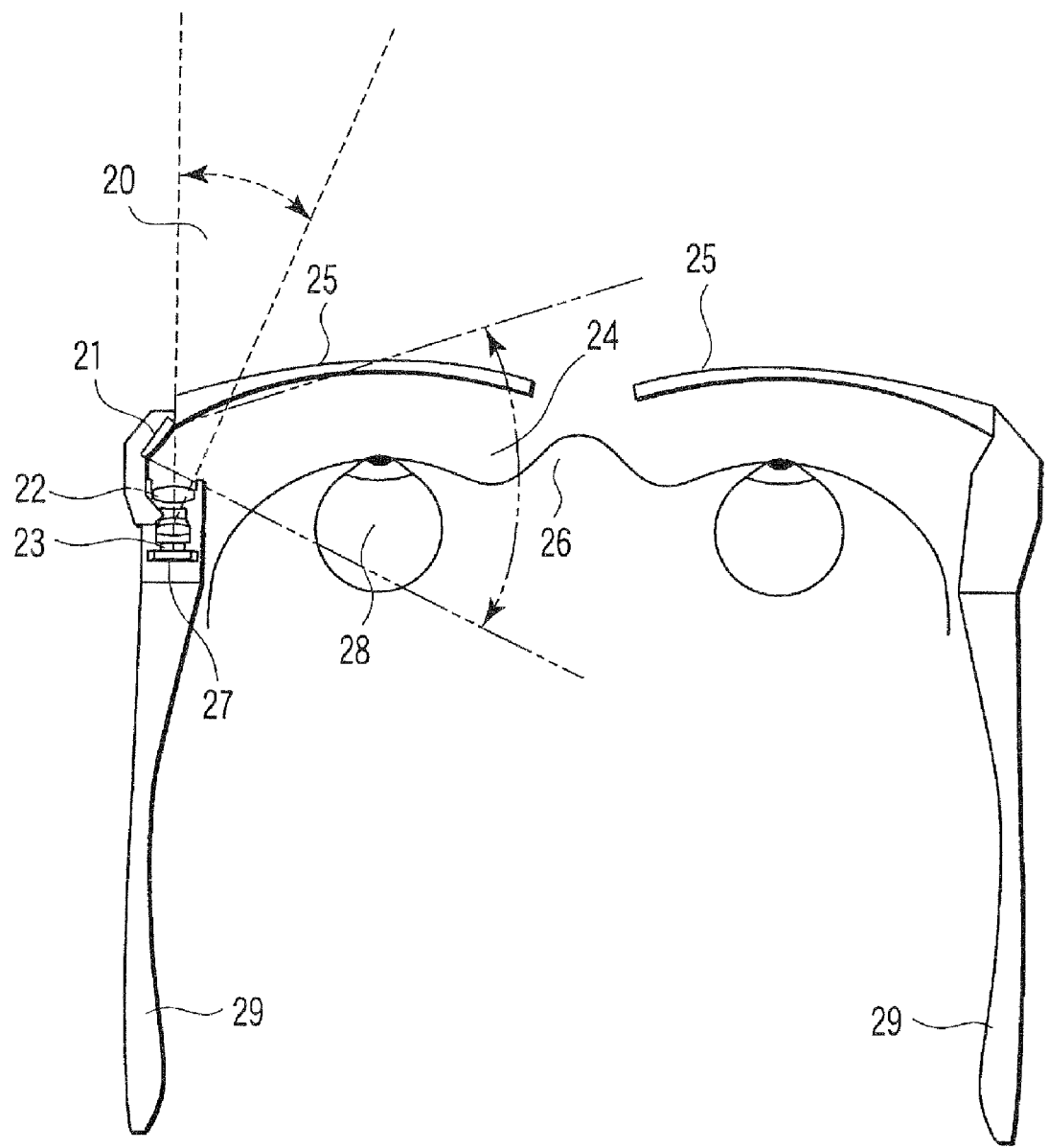
FIG. 1 is a horizontal sectional view of a head-mounted camera according to a first embodiment of the present invention.
Figure 2:
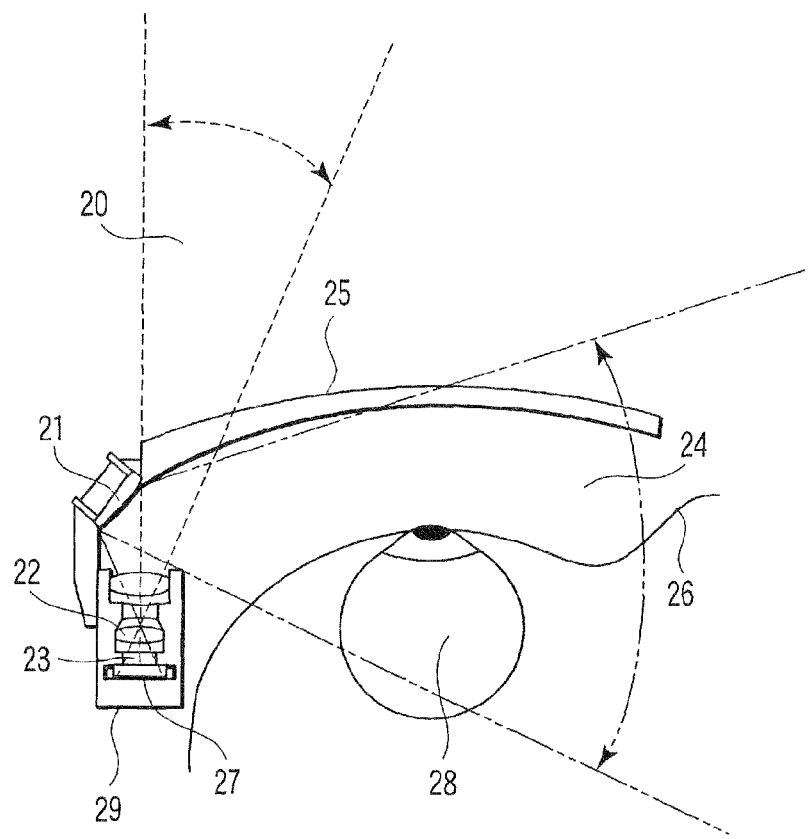
FIG. 2 is an enlarged view showing a part of FIG. 1.
Figure 3:
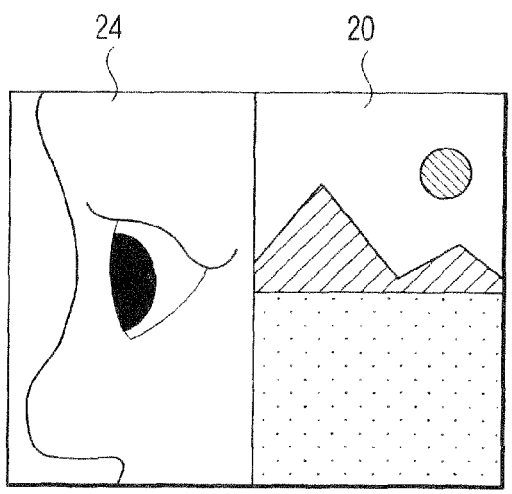
FIG. 3 is a picked-up image diagram according to the first embodiment.

FIG. 1 is a horizontal sectional view of a head-mounted camera according to a first embodiment of the present invention. The head-mounted camera of the first embodiment is provided with an image sensor 27, an imaging lens 22, and a convex reflective mirror (first mirror) 21. The image sensor 27 is disposed on a bow portion of a left-hand mounting jig 29, out of left- and right-hand glasses-type mounting jigs 29. The imaging lens 22 is provided for image formation on the image sensor 27. The first mirror 21 is located in a position such that it can laterally catch an eyeball at an angle within a range from 30° to 60°, preferably at 45°, to the imaging lens 22, and reflects a beam of light that covers about half the angle of view of the imaging lens 22. Further, a low-pass/infrared cut filter 23 is located in front of the image sensor 27. Furthermore, the mounting jigs 29, which are glasses-shaped, are fitted individually with mounting jig lenses 25, and they can be stably mounted on a face with the aid of nosepieces (not shown). FIG. 2 is an enlarged view showing a part of FIG. 1. Further, FIG. 3 is a picked-up image diagram showing images picked up by the image sensor 27. The left-hand half of the diagram is an image based on an eyeball imaging side view 24, while the right-hand half is an image based on an environment imaging side view 20.

Figure 4:
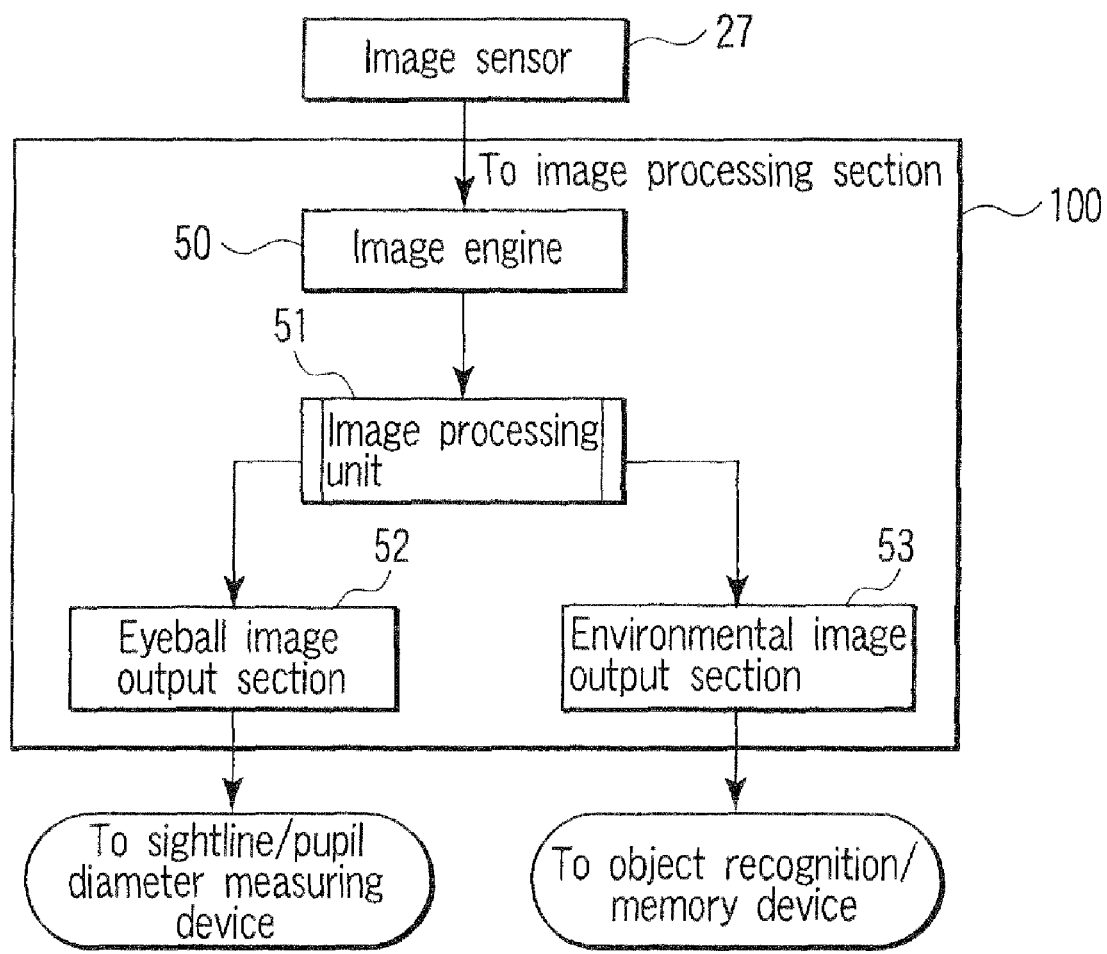
FIG. 4 is a diagram showing a configuration of an image processing section 100 that generates an image from an imaging signal from an image sensor 27.

FIG. 4 shows a configuration of an image processing section 100 that generates an image from an imaging signal from the image sensor 27. The image processing section 100 is provided with an image engine 50, image processing unit 51, an eyeball image output section 52, and an environmental image output section 53.

In the description here, a configuration composed of the imaging tens 22, low-pass/infrared cut filter 23, image sensor 27, and image processing section 100 is defined as a camera section.

The following is a description of the operation of the above configuration. A subject image (not shown) that exists in front of the mounting jigs 29 is formed by about half the view of the imaging lens 22 and picked up by the image sensor 27. The image picked up in this manner is called an environmental image. The image acquisition range for this process is represented by the environment imaging side view 20 in FIGS. 1 and 2.

On the other hand, the remaining half of the view of the imaging lens 22 is used when the periphery of an eye is image-acquired from a side of the face by means of the first mirror 21 and is called the eyeball imaging side view 24 in FIGS. 1 and 2. A convex mirror is used as the first mirror 21 in order to increase the angle of view. It has the same effect as a close-up lens and is configured for close-up image acquisition. Thus, it is possible to pick up an image that is focused on both the region around the adjacent eye and a subject that exists at a frontal distance from the glasses.

The image picked up by the image sensor 27 is input to the image engine 50 of the image processing section 100 and converted into predetermined image data. The image processing unit 51 performs processing such as cutting-out of regions for the environmental image and an eyeball image, rotation, enlargement, and contraction of the images, etc. The eyeball image output section 52 and the environmental image output section 53 output the eyeball image and the environmental image, respectively, in desired image formats. The output eyeball image is input to a sightline/pupil diameter measuring device. Hemisphere images of eyeballs are used to determine the dominant eye, left or right, whether the eyes are open or closed, etc. On the other hand, the output environmental image is input to an object recognition/memory device.

Although the two images are separately output in this case, an image generated in the image engine 50 may be output directly. Although the eyeball image and the environmental image are input to the sightline/pupil diameter measuring device and the object recognition/memory device, respectively, in this case, moreover, they may alternatively be input to a communication device that distributes signals to wireless and wired networks.

According to the configuration described above, the view image and the eyeball image can be simultaneously recorded by means of the single image sensor, so that the number of necessary cameras can be reduced. Thus, if the first mirror 21 is set on the bow portion of the mounting jig 29 so that half the view of the imaging lens 22 can be reflected by the first mirror 21, the view can be bent to enable close-up image acquisition, whereby the face, especially regions near the eyeball, can be image-acquired. At the same time, an environmental image in front of a user's head is acquired by the other half of the view of the imaging lens 22.

It is to be understood that various configurations of the embodiment of this invention are subject to various modifications and changes. For example, the lenses of the glasses shown in FIGS. 1 and 2 are myopic lenses (concave lenses). Alternatively, however, they may be replaced with no-power lenses or a head-mounted display (HMD). The image processing section and the image sensor may be connected wirelessly.

Figure 5:
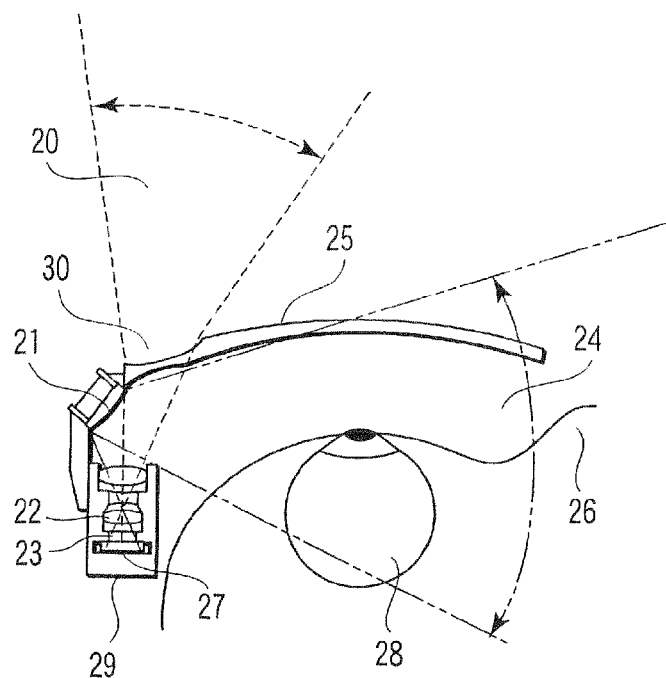
FIG. 5 is a view showing a first modification of the first embodiment.

FIG. 5 shows a first modification of the first embodiment, which is configured so that a concave lens serves for focus and view-angle correction. In the first embodiment, the convex mirror is used as the first mirror (reflective mirror) 21 in order to increase the angle of view. Alternatively, however, both the eyeball image and a front view image may be configured to be focused by partially changing the curvature of the mounting jig lens 25 (e.g., by disposing a concave lens area 30 in an optical transmission path in the oriented direction (front view image) of the head).

Figure 6:
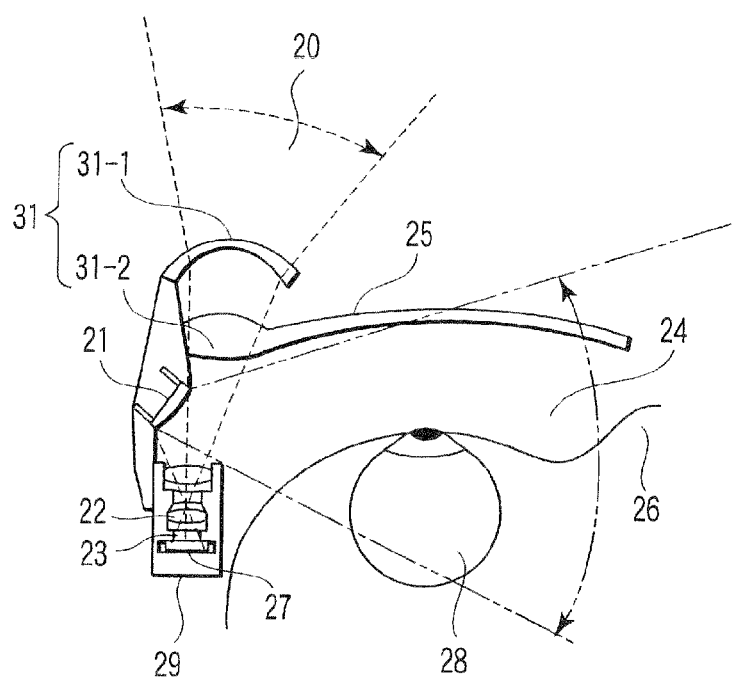
FIG. 6 is a view showing a second modification of the first embodiment.

FIG. 6 shows a second modification of the first embodiment, in which an afocal optical system is used for a wide-angle configuration. As shown in FIG. 6, the environmental image can be acquired in a wide field of view by adding negative lenses or wide-conversion lenses 31 (concave lens 31-1 and convex lens area 31-2 in FIG. 6) incorporated in afocal manner to the region of the mounting jig lens 25.

Figure 7:
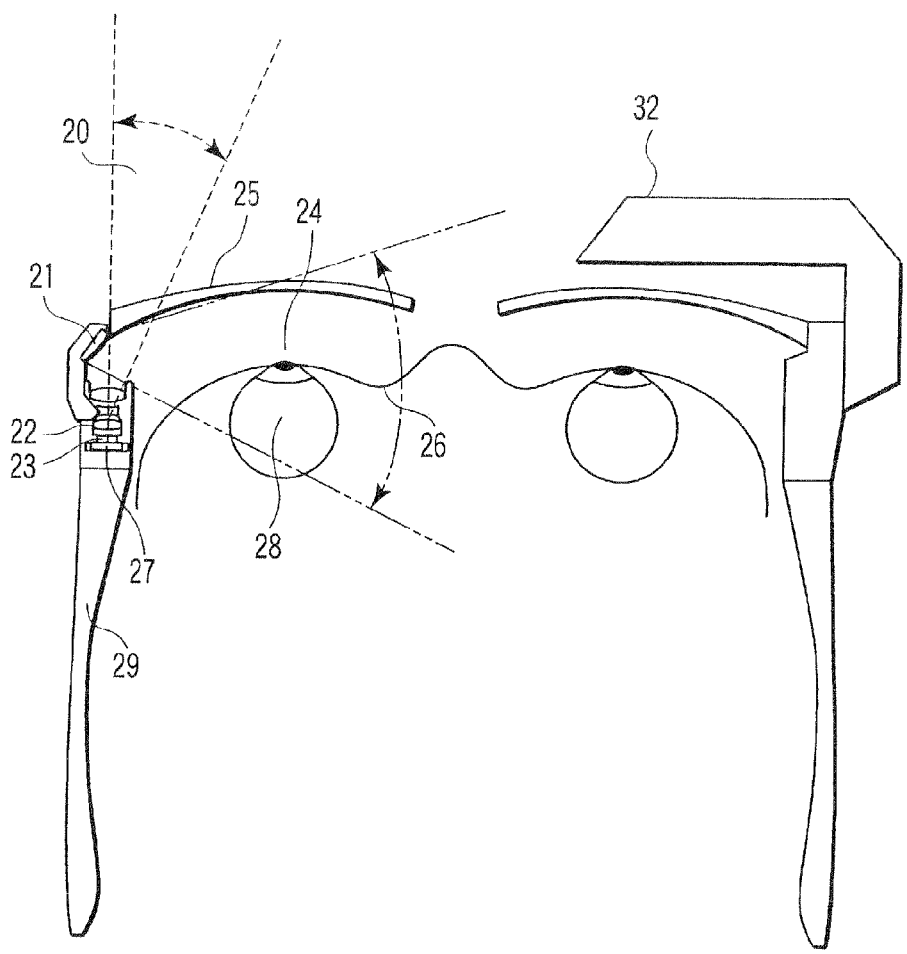
FIG. 7 is a view showing a third modification of the first embodiment.

FIG. 7 shows a third modification of the first embodiment. The present embodiment is characterized in that a head-mounted display (HMD) 32 is set in front of the opposite eyeball.

Figure 8:
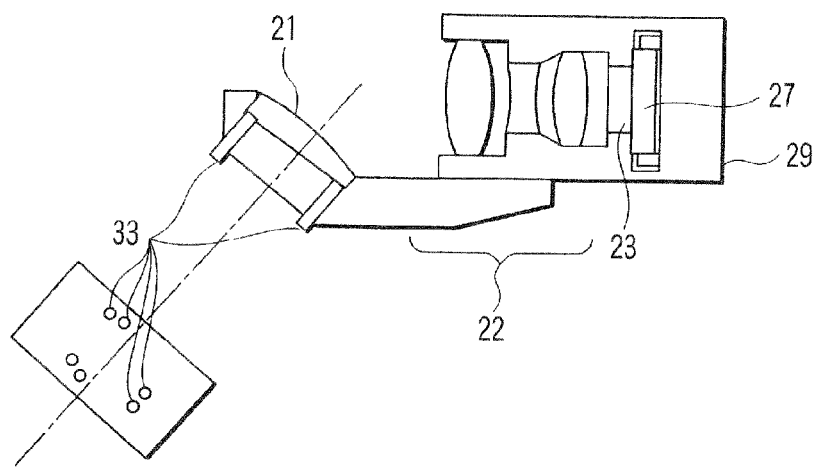
FIG. 8 is an enlarged view of a camera section according to the present embodiment.

FIG. 8 is an enlarged view of a camera section according to the present embodiment. As shown in FIG. 8, adjusting screws (optical axis adjusters) 33 formed of, for example, six push-pull screws, are provided for adjusting the position of the first mirror 21 so that the eyeball image can be acquired.

Second Embodiment

Figure 9:
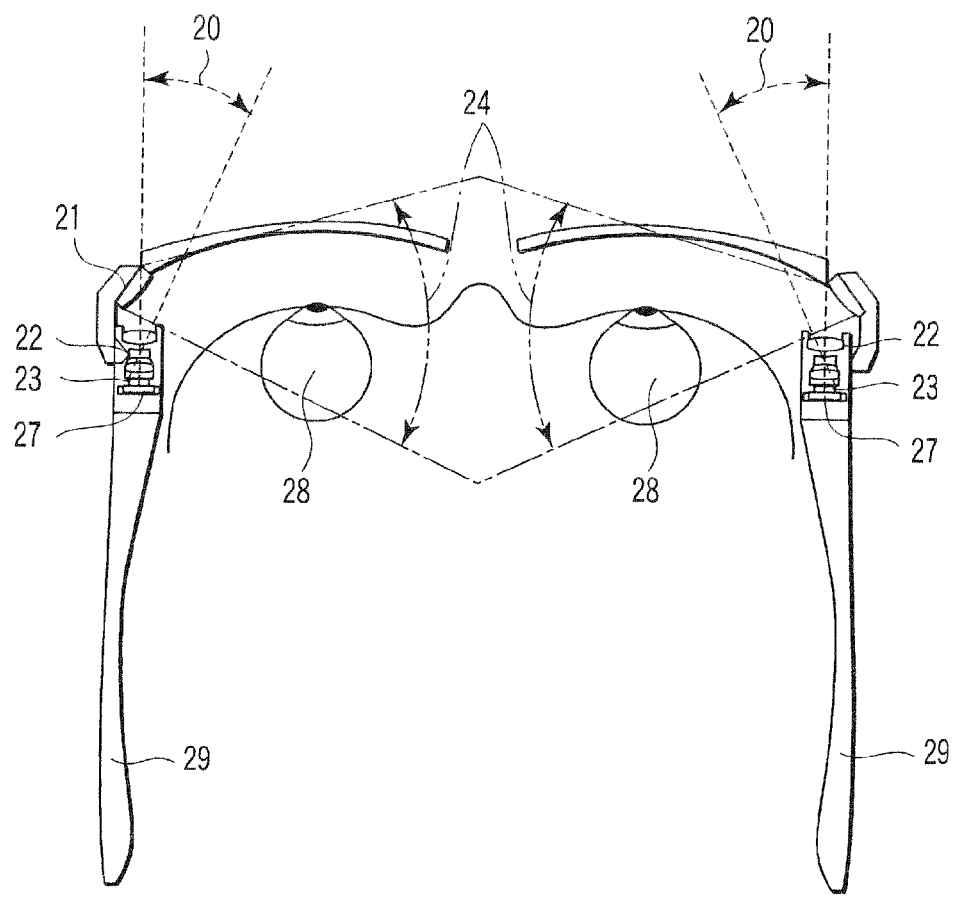
FIG. 9 is a horizontal sectional view of a head-mounted camera according to a second embodiment of the present invention.

FIG. 9 is a horizontal sectional view of a head-mounted camera according to a second embodiment of the present invention. The second embodiment is a binocular head-mounted camera in which a camera section is provided on not only a bow portion of a right-hand mounting jig 29 in the first embodiment, but also on a bow portion of a left-hand mounting jug 29. In this case, mirrors of the individual camera sections are arranged bisymmetrically. According to this configuration, images can be acquired from both sides, left and right, so that convergence measurement and estimation of the line of sight can be preformed with ease.

Since the environmental image can be acquired stereoscopically, moreover, a stereoscopic configuration of a subject (not shown) can also be caught based on a three-dimensional configuration.

Figure 10:
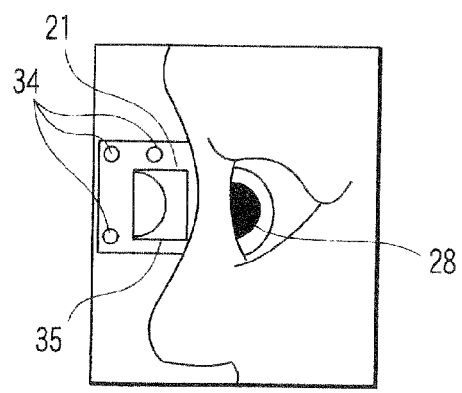
FIG. 10 is a view showing a configuration for accurate measurement of the relative positions of both eyes in the binocular head-mounted camera.

FIG. 10 shows a configuration for accurate measurement of the relative positions of both eyes in the binocular head-mounted camera constructed in this manner. Specifically, if two cameras are mounted on glasses that are worn by a user, the relative positions of the two cameras may possibly fluctuate owing to a distortion of the glasses. As shown in FIG. 10, therefore, a plurality of markers 34 may be arranged in predetermined positional relationships with a first mirror 21 of the mounting jig 29 on which one of the cameras is mounted. If this is done, fluctuations of the positional relationship between the left- and right-hand cameras that are attributable to the distortion of the glasses can be detected by picking up images of the markers by means of the other camera.

Third Embodiment

Figure 11:
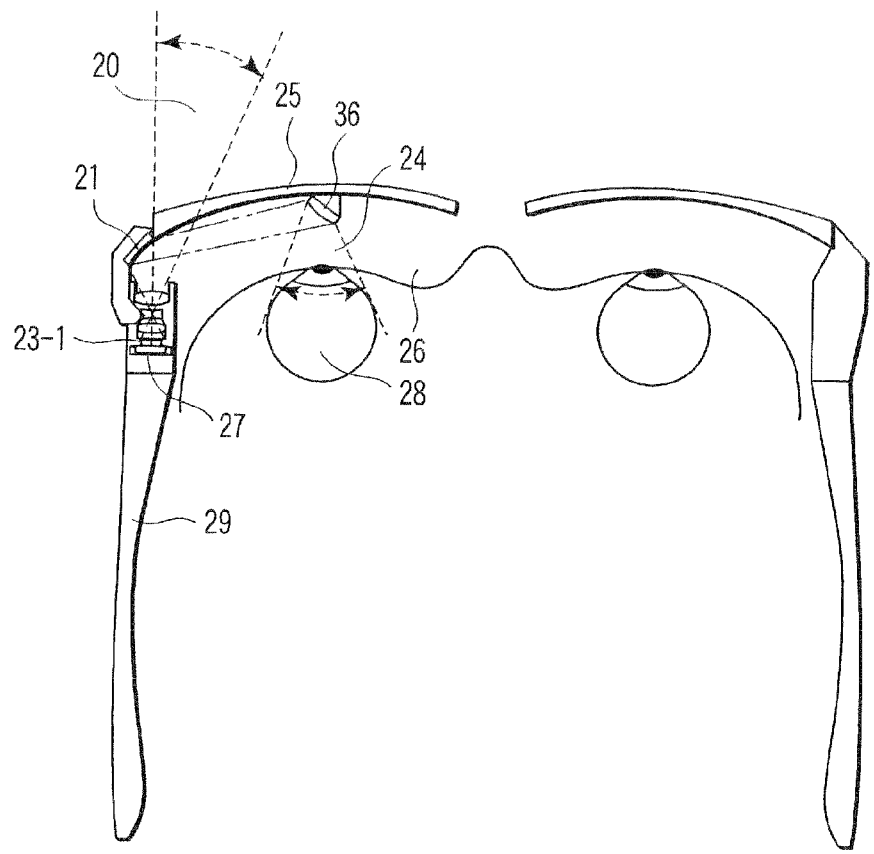
FIG. 11 is a horizontal sectional view of a head-mounted camera according to a third embodiment of the present invention.
Figure 12:
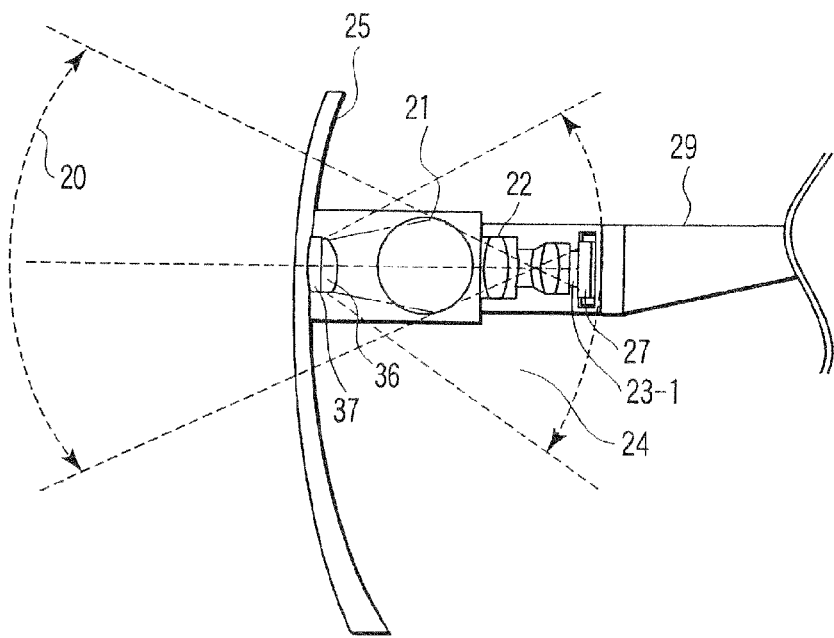
FIG. 12 is an enlarged side view of a camera section of FIG. 11.

FIG. 11 is a horizontal sectional view of a head-mounted camera according to a third embodiment of the present invention. FIG. 12 is an enlarged side view of a camera section of FIG. 11. The third embodiment is characterized in that a flat-concave mirror lens as a first mirror 21 is used to constrict a luminous flux, and that a convex mirror as a second mirror 36 is disposed in a position on a mounting jig lens 25 opposite an eyeball 28 in order to increase the angle of view.

The second mirror 36 is fixed to the mounting jig lens 25 by an adjustment jig 37 that is formed of a thermoplastic resin. Since the pupil position varies depending on the user, the adjustment jig 37 is used to change the position of the second mirror 36, that is, an imaging range. Specifically, the second mirror 36 may be supported by the adjustment jig 37 so that heat can be applied to the adjustment jig 37 of the thermoplastic resin to adjust the angle of the second mirror 36 for each user. The first mirror may be supported by the adjustment jig so that the same adjustment as aforesaid can be performed.

Further, a filter 23-1 used in this case has a low-pass/infrared cutoff function for an environment imaging side view and a visible light cutoff/infrared transmission function for an eyeball imaging side view.

Figure 13:
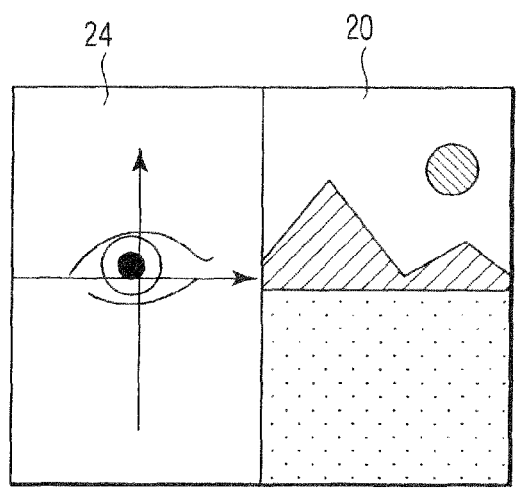
FIG. 13 is a picked-up image diagram according to the third embodiment.

A flat-convex mirror lens for use as the second mirror 36 is a lens that has a mirror surface on its flat side and bears positive power. An eyeball front image (front pupil image) can be acquired with this configuration. FIG. 13 is a picked-up image diagram for this point of time. The left-hand half of the diagram is an image based on an eyeball imaging side view 24, while the right-hand half is an image based on an environment imaging side view 20.

According to the third embodiment, both an eyeball image and an image observed by a mount can be picked up in one picture. Further, the convergence, pupil diameter fluctuations, line of sight, etc. can be measured as a stereoscopic video image of a portion toward which the face is then mainly directed is acquired.

Fourth Embodiment

Figure 14:
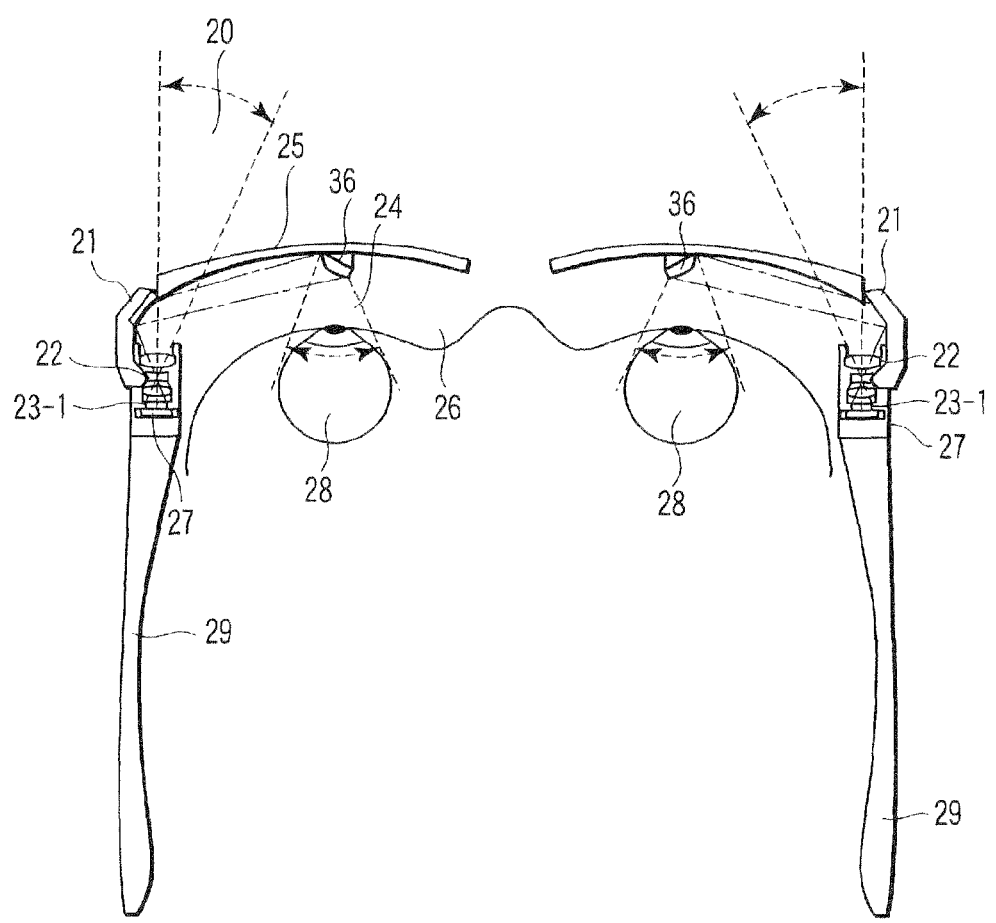
FIG. 14 is a horizontal sectional view of a head-mounted camera according to a fourth embodiment of the present invention.

FIG. 14 is a horizontal sectional view of a head-mounted camera according to a fourth embodiment of the present invention. The fourth embodiment is a binocular head-mounted camera in which a camera section is provided on not only a bow portion of a right-hand mounting jig 29 in the third embodiment, but also on a bow portion of a left-hand mounting jig 29. In this case, mirrors of the individual camera sections are arranged bisymmetrically. According to this configuration, images can be acquired from both sides, left and right, so that convergence measurement and estimation of the line of sight can be performed with ease.

Since the environmental image can be acquired stereoscopically, moreover, a stereoscopic configuration of a subject (not shown) can also be caught based on a three-dimensional configuration.

Fifth Embodiment

Figure 15:
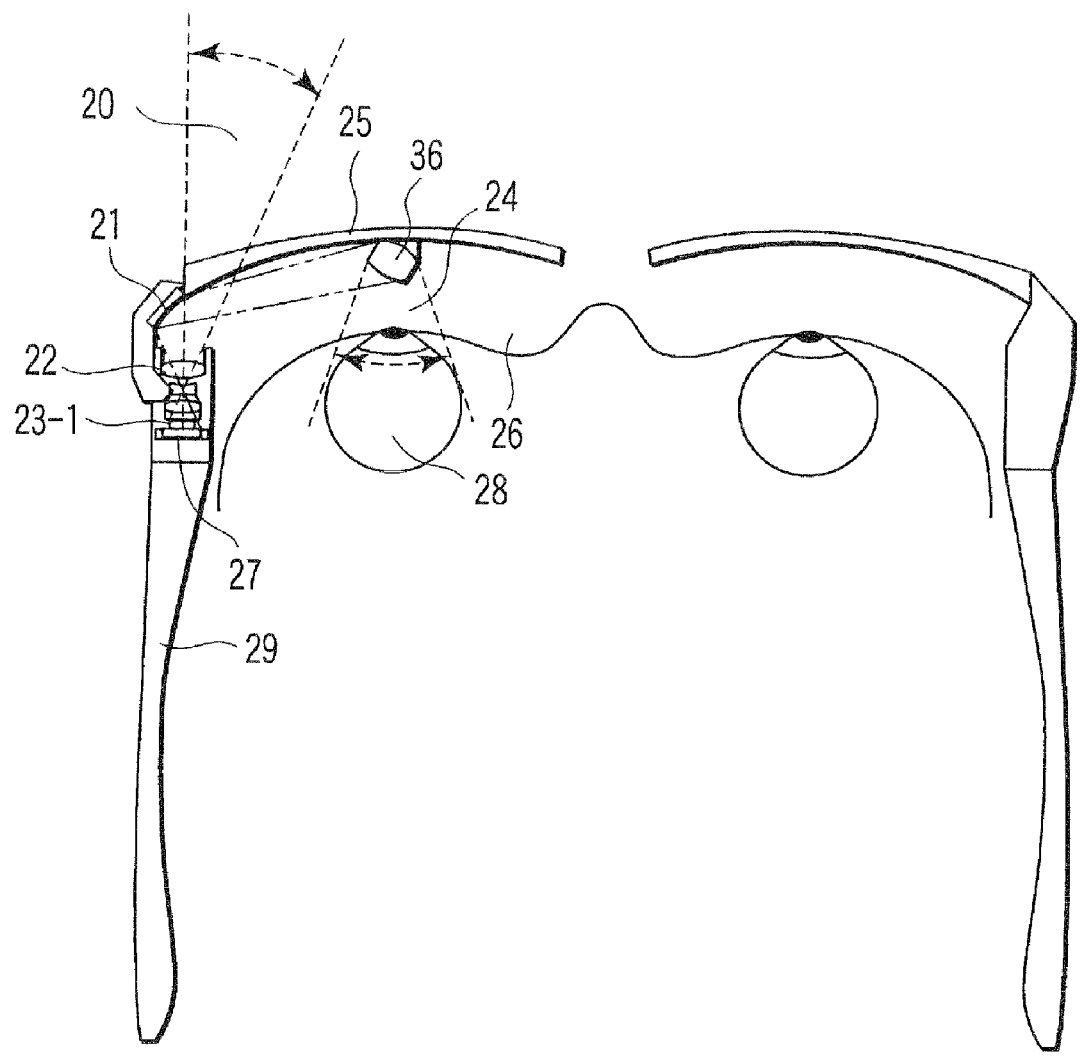
FIG. 15 is a horizontal sectional view of a head-mounted camera according to a fifth embodiment of the present invention.
Figure 16:
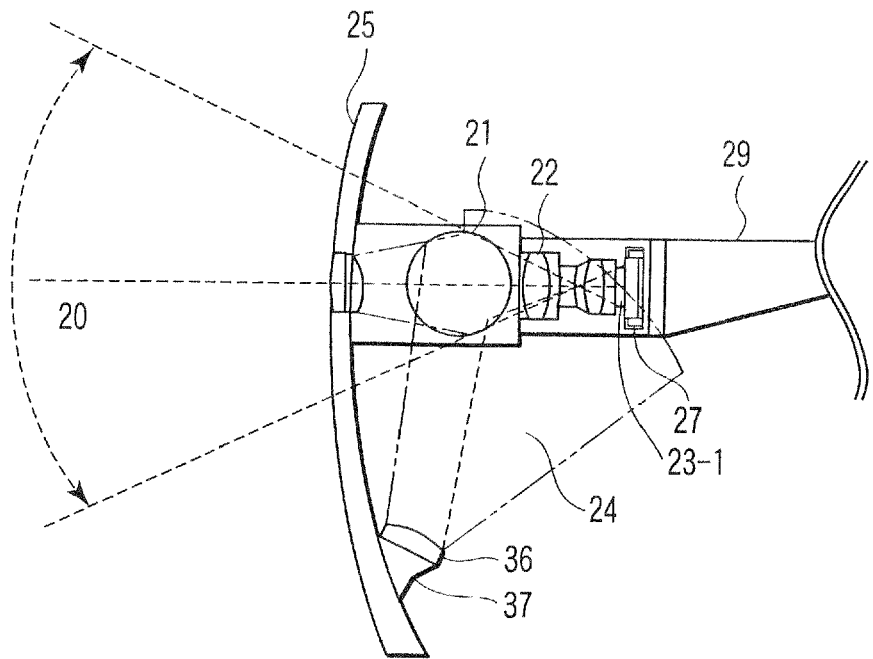
FIG. 16 is an enlarged side view of a camera section FIG. 15.
Figure 17:
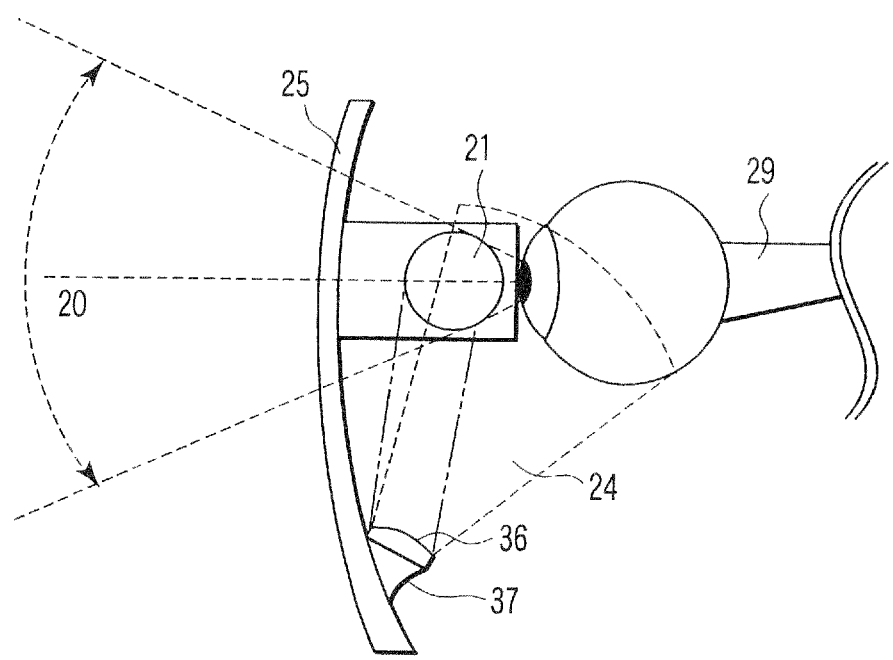
FIG. 17 is a view showing a position of an eyeball 28 in the configuration shown in FIG. 16.

FIG. 15 is a horizontal sectional view of a head-mounted camera according to a fifth embodiment of the present invention. Further, FIG. 16 is an enlarged side view of a camera section of FIG. 15. Furthermore, FIG. 17 illustrates a position of an eyeball 28 in the configuration shown in FIG. 16.

In the third embodiment described before, the second mirror 36 is located just in front of the eyeball, so that it may intercept a user's view, in some cases. Thereupon, the fifth embodiment is characterized in that a second mirror 36 is disposed on a lower part of a mounting jig lens 25, not in the position on the mounting jig lens 25 opposite the eyeball 28. In this configuration, an image from the eyeball 28 is reflected upward by the second mirror 36 after it is directed into the second mirror 36, and the resulting reflected light lands on a first mirror 21. The first mirror 21 reflects the reflected light so that it is incident on an image sensor 27.

Figure 18:
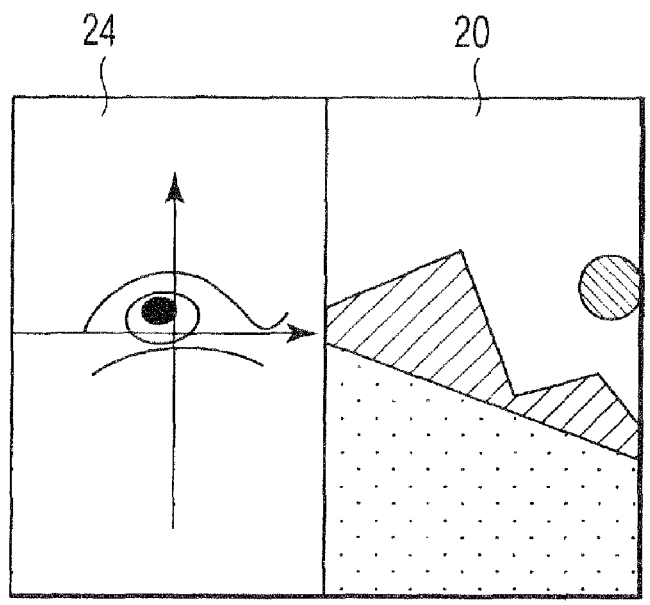
FIG. 18 is a picked-up image diagram according to the fifth embodiment.

FIG. 18 is a picked-up image diagram according to the fifth embodiment. In the case of the configuration of FIGS. 16 and 17, an image obtained in an eyeball imaging side view 24 inevitably undergoes image rotation based on the reflection angle of the reflective mirror. Therefore, the image sensor 27 is located at an angle corresponding to the image rotation around the optical axis. Thus, as shown in FIG. 18 (A), an inclined picked-up image is obtained in an environment imaging side view 20, while a correct picked-up image is obtained in the eyeball imaging side view 24. Preferably, in this case, an environment-side picked-up image should be rotated based on an epiphora line of a stereo view.

Alternatively, moreover, the image acquired by the image sensor may be rotated after images are profiled in individual image acquisition areas based on coordinate axes for measuring motions of the line of sight in vertical and horizontal directions by rotating the image or the epiphora line of the stereo view.

Figure 19:
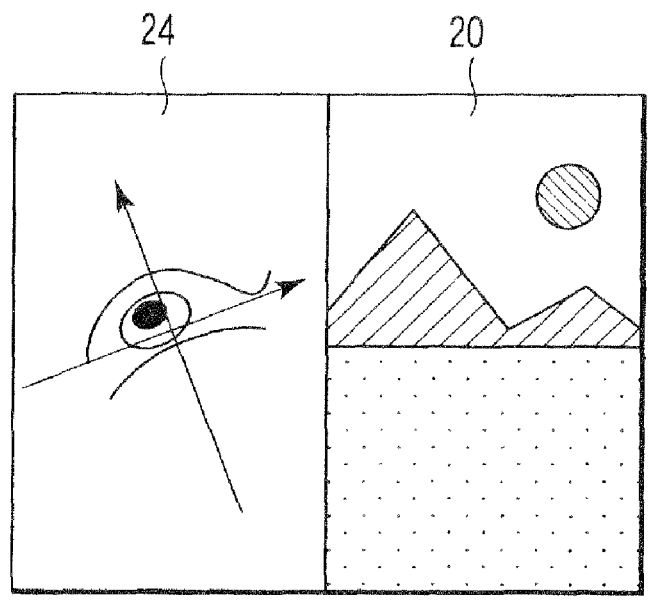
FIG. 19 shows a picked-up image obtained without tilting an image sensor.

If the environment-side picked-up image is to be given priority, furthermore, an eyeball-side picked-up image may be rotated by image processing so that the image sensor itself can be disposed along the epiphora line without being tilted. FIG. 19 shows a picked-up image obtained without tilting the image sensor. In this case, an inclined picked-up image is obtained in the eyeball imaging side view 24, while a correct picked-up image can be obtained in the environment imaging side view 20.

Sixth Embodiment

FIG. 20 is a horizontal sectional view of a head-mounted camera according to a sixth embodiment of the present invention. The sixth embodiment is a binocular head-mounted camera in which a camera section is provided on a bow portion of a right-hand mounting jig 29 as well as on a bow portion of a left-hand mounting jig 29. In this case, mirrors of the individual camera sections are arranged bisymmetrically. According to this configuration, images can be acquired from both sides, left and right, so that convergence measurement and estimation of the line of sight can be performed with ease.

APPENDIX

It is to be understood that various configurations of the embodiment of this invention are subject to various modifications and changes. The convex mirror for use as the second mirror may be replaced with a flat-concave mirror lens that has a mirror surface on the flat side of a flat-concave lens or a combination of a concave mirror and a convex mirror or a combination of a flat-convex mirror lens and a flat-concave mirror lens with similar positive-negative power distributions.

The use of the flat-concave mirror lens and the flat-convex mirror lens is effective for the protection of evaporated surface of the mirror, in particular. In contrast with this, the combination of the concave mirror and the convex mirror has an advantage of being free from color aberration, since it is a combination of reflective surfaces alone.

Further, a sharper image can be picked up from an eyeball with a curvature that fits the user by using a variable-focus mirror lens or the like that is stuffed with a liquid refractive material and has a concave variable film surface and a flat mirror surface. Alternatively, an electrostatic variable-focus mirror may be used to adjust the optical axis and the focal length, thereby fitting the mounting jigs to the head and adjusting the image acquisition position to the user's eyeball position.

According to the present invention, there may be provided an image pickup apparatus capable of picking up an environmental image and an eyeball image while reducing the number of cameras used.

What is claimed is:

1. An image pickup apparatus comprising:
an imaging optical system;
an image sensor which picks up a subject image formed by the imaging optical system; and
a view division optical system which divides a view picked up by the image sensor into an environment imaging side view and an eyeball imaging side view,
wherein the eyeball imaging side view is a view in which an image of a periphery of an eye is acquired from a lateral side of a face by means of the view division optical system, and
wherein the view division optical system comprises a reflective mirror which is positioned such that an optical axis of the imaging optical system is in between an entirety of the reflective mirror and the face.

2. The image pickup apparatus according to claim 1, wherein the reflective mirror is located prior to the imaging optical system at a predetermined inclination with respect to the imaging optical system, and wherein the reflective mirror divides a view of the imaging optical system into at least two parts.

3. The image pickup apparatus according to claim 2, wherein the reflective mirror is formed of an optical system with negative power.

4. The image pickup apparatus according to claim 3, wherein the reflective mirror is a convex mirror.

5. The image pickup apparatus according to claim 3, wherein the reflective mirror comprises a transmissive-reflective mirror lens having a concave refractive surface and at least a reflective surface with a radius of curvature larger than that of the concave refractive surface.

6. The image pickup apparatus according to claim 2, wherein the reflective mirror is formed of an optical system with positive power.

7. The image pickup apparatus according to claim 6, wherein the reflective mirror is a concave mirror.

8. The image pickup apparatus according to claim 6, wherein the reflective mirror comprises a transmissive-reflective mirror lens having a convex refractive surface and at least a reflective surface with a radius of curvature smaller than that of the convex refractive surface.

9. The image pickup apparatus according to claim 1, further comprising a bent optical system which picks up an image of the eye for the view divided by the view division optical system.

10. The image pickup apparatus according to claim 9, wherein the reflective mirror is located prior to the imaging optical system at a predetermined inclination with respect to the imaging optical system, and the reflective mirror divides a view of the imaging optical system into at least two parts, and wherein the bent optical system comprises a second reflective mirror which further bends a halved view at a predetermined angle.

11. The image pickup apparatus according to claim 1, further comprising:
a second imaging optical system;
a second image sensor which picks up a subject image formed by the second imaging optical system; and
a second view division optical system which divides a view picked up by the second image sensor into a second environment imaging side view and a second eyeball imaging side view.

12. The image pickup apparatus according to claim 11, further comprising a marker which detects a positional fluctuation between the image sensor and the second image sensor.

13. The image pickup apparatus according to claim 11, further comprising a marker which detects a positional fluctuation between the view division optical system and the second view division optical system.

14. The image pickup apparatus according to claim 11, wherein at least one of the image sensor and the second image sensor is located opposite each other so that (i) the image sensor is configured to pick up an image of at least a part of the second imaging optical system, the second image sensor and the second view division optical system, and/or (ii) the second image sensor is configured to pick up an image of at least a part of the imaging optical system, the image sensor and the view division optical system.

15. The image pickup apparatus according to claim 1, wherein the view division optical system is fixed to a mounting jig worn by an observer.

16. The image pickup apparatus according to claim 1, wherein the view division optical system is provided in a part of a frame of glasses or of a lens.

17. The image pickup apparatus according to claim 1, wherein the view division optical system is provided in a part of a head-mounted display.

18. The image pickup apparatus according to claim 1, wherein the eyeball imaging side view is a view in which the image of the periphery of the eye is acquired from one of a lateral left side and a lateral right side of the face by means of the view division optical system.

19. The image pickup apparatus according to claim 1, wherein the image sensor acquires an eyeball image by means of the eyeball imaging side view through the view division optical system.

* * * * *